United States Patent [19]

Ford et al.

[11] Patent Number: 4,605,770

[45] Date of Patent: * Aug. 12, 1986

[54] NONCYCLIC POLYALKYLENE POLYAMINES BY THE REACTION OF AN ALKANOLAMINE COMPOUND AND AN ALKYLENEAMINE COMPOUND IN THE PRESENCE OF A GROUP IIA OR GROUP IIIB METAL ACID PHOSPHATE CATALYST

[75] Inventors: Michael E. Ford, Center Valley; Thomas A. Johnson, Orefield, both of Pa.

[73] Assignee: Air Products and Chemicals, Inc., Allentown, Pa.

[*] Notice: The portion of the term of this patent subsequent to Mar. 25, 2003 has been disclaimed.

[21] Appl. No.: 564,594

[22] Filed: Dec. 22, 1983

[51] Int. Cl.$^4$ ............................................. C07C 85/06
[52] U.S. Cl. .................................. 564/479; 564/478; 564/469; 564/503; 564/511; 564/512
[58] Field of Search ............... 564/479, 478, 469, 503, 564/511, 512

[56] References Cited

U.S. PATENT DOCUMENTS

| | | |
|---|---|---|
| 3,714,259 | 1/1973 | Lichtenwalter et al. ........... 564/480 |
| 3,755,447 | 8/1973 | Klemann et al. .................... 564/461 |
| 3,766,184 | 10/1973 | Johansson et al. .................. 544/358 |
| 4,014,933 | 3/1977 | Boettger et al. .................... 564/479 |
| 4,036,881 | 7/1977 | Brennan et al. .................... 564/479 |
| 4,044,053 | 8/1977 | Brennan et al. .................... 564/479 |
| 4,316,840 | 2/1982 | Ford et al. ......................... 564/479 |
| 4,316,841 | 2/1982 | Ford et al. ......................... 564/479 |
| 4,324,917 | 4/1982 | McConnell et al. ................ 564/479 |
| 4,405,784 | 9/1983 | Wells .......................... 219/121.0 PV |
| 4,446,320 | 5/1984 | Eskinazi et al. ................... 564/479 |

*Primary Examiner*—Charles F. Warren
*Assistant Examiner*—John A. Sopp
*Attorney, Agent, or Firm*—Michael Leach; James C. Simmons; E. Eugene Innis

[57] ABSTRACT

A process for preparing predominantly noncyclic polyalkylene polyamine compounds is disclosed wherein an alkanolamine compound and an alkyleneamine compound in a molar ratio of alkanolamine compound:alkyleneamine compound of 1:5 to 3:1, preferably less than 1, is reacted in the presence of a catalytically effective amount of a Group IIA or Group IIIB metal acid phosphate at a temperature from about 200° to 400° C. under a pressure sufficient to maintain the reaction mixture substantially in liquid phase.

40 Claims, No Drawings

NONCYCLIC POLYALKYLENE POLYAMINES BY THE REACTION OF AN ALKANOLAMINE COMPOUND AND AN ALKYLENEAMINE COMPOUND IN THE PRESENCE OF A GROUP IIA OR GROUP IIIB METAL ACID PHOSPHATE CATALYST

TECHNICAL FIELD

This invention relates to the preparation of polyalkylene polyamines, particularly noncyclic polyalkylene polyamines.

BACKGROUND OF THE INVENTION

Low molecular weight polyethylene polyamines are used in a wide variety of applications such as corrosion inhibitors, fabric softeners, lubricating oil additives, fungicides and many others. Despite the utility of polyethylene polyamines, they are currently obtained only as by-products of ethylenediamine manufactured by the reaction of ethylenedichloride with excess ammonia. Since the polyamines are by-products of ethylenediamine preparation, the supply and quality of available polyethylene polyamines are often variable. Generally, high yields of cyclic polyethylene polyamines, e.g., piperazine, aminoethylpiperazine and the like, are produced although it is the noncyclic polyamines such as diethylenetriamine, triethylenetetramine and higher homologs that are commercially desirable. Moreover, since sodium chloride is co-produced in large quantities, separation of the products from the sodium chloride and the handling and disposal of this corrosive inorganic salt requires special measures.

The prior art discloses various attempts to circumvent these difficulties and to provide controllable efficient routes to polyethylene polyamines:

U.S. Pat. No. 3,714,259 discloses the preparation of linear polyethylene amines by contacting ethanolamine with ethylenediamine compounds in the presence of hydrogen and a hydrogenation catalyst. An example of a hydrogenation catalyst is nickel containing copper and chromium components. Significant amounts of water are included in the feedstock, namely 25-50 wt% based on the combined starting ethylenediamine and monoethanolamine.

U.S. Pat. No. 3,766,184 discloses the reductive amination of monoethanolamine by metallic catalyst of iron and nickel and/or cobalt in the presence of hydrogen.

U.S. Pat. No. 4,036,881 discloses the preparation of polyalkylene polyamines by reacting an alkanolamine with an alkyleneamine compound in the presence of a phosphorus containing substance selected from the group consisting of acidic metal phosphates, phosphoric acid compounds and anhydrides and the phosphate esters.

U.S. Pat. No. 4,044,053 is somewhat similar to the '881 patent except that the alkyleneamine compound is present in an excess amount and a diol is used in place of the alkanolamine.

U.S. Pat. No. 4,314,083 discloses a process for selectively preparing predominantly noncyclic polyalkylene polyamines by reacting an alkanolamine with an alkyleneamine compound in the presence of a salt of a nitrogen or sulfur containing substance or the corresponding acid.

U.S. Pat. No. 4,324,917 discloses ion exchange resins containing phosphonic acid functionality as catalysts for the production of polyethylene polyamines by alkylation of alkyleneamines such as ethylenediamine with alkanolamines such as monoethanolamine.

In addition, U.S. Pat. No. 4,405,784 discloses strontium diorthophosphate as catalyst for acid catalyzed organic condensation reactions, for example the conversion of hydroxyethylpiperazine to triethylenediamine.

Although the prior art does show good selectivities to noncyclic polyamine products, attainment of these selectivies usually requires reaction of a molar deficiency of the alkanolamine with a molar excess of the alkyleneamine. Conversely, if a molar excess of the alkanolamine is reacted with a molar deficiency of the alkyleneamine, selectivities to noncyclic polyamines are low, generally less than 50 wt%.

Therefore, a deficiency of the prior art is the requirement of an excess of alkyleneamine, such as ethylenediamine, to generate predominently noncyclic polyamines. Since higher noncyclic polyamines are formed by successive alkylations of alkyleneamine by the alkanolamine, inclusion of excess alkyleneamine dilutes the reaction, and imposes several disadvantages. For instance, in order to obtain a specified level of polyamine production, the feed and reactor systems must have a greater capacity than if the excess alkyleneamine were not included. Additionally, the system for product separation and purification must be larger to remove and recycle the excess alkylenediamine than if the diluent were not included.

The prior art phosphate catalysts suffered from the deficiency that their solubility in the reaction mixture limits process options, since a soluble catalyst cannot be readily localized in a reaction zone, such as a packed bed reactor, and complicates product isolation and recovery, since the catalyst must be separated from the reaction effluent and recycled to the reaction zone.

SUMMARY OF THE INVENTION

It has been found that noncyclic, or linear and branched, polyalkylene polyamines are produced in good yield directly by reacting an alkanolamine compound and an alkyleneamine compound, preferably in a molar ratio of alkanolamine:alkyleneamine which is from 3:1 to 1:5, especially less than 1, in the presence of a catalytically effective amount of a Group IIA or Group IIIB metal acid phosphate at a temperature sufficient to effect reaction between the alkanolamine compound and alkyleneamine compound under a pressure sufficient to maintain the reaction mixture essentially in liquid phase.

As an advantage of the invention, the process produces predominantly noncyclic polyalkylene polyamines and in one embodiment does not require reacting a molar excess of alkyleneamine with a molar deficiency of alkanolamine to do so. Predominantly noncyclic polyalkylene polyamines means greater than about 50 wt% of linear and branched polyalkylene polyamines in the total polyamines product.

A wide range of noncylic polyamines is produced without the necessity of including an inert diluent or an excess alkyleneamine in the feed and removing it from the reaction product.

As a further advantage, the use of Group IIA and Group IIIB metal acid phosphates as catalysts avoids problems associated with co-production of stoichiometric quantities of an inorganic salt.

Furthermore, in contrast to many Group IA acid phosphates, Group IIA and IIIB metal acid phosphates are insoluble in the reaction medium. Thus, under conditions for operation of this process, Group IIA and IIIB metal acid phosphates are insoluble solids that are easily localized in a fixed bed or continuous stirred tank reactor. Isolation of polyamine products, particularly in continuous processes, is therefore readily accomplished.

DETAILED DESCRIPTION OF THE INVENTION

The invention relates to a process for synthesizing predominantly noncyclic polyalkylene polyamines, particularly linear and branched polyethylene polyamines such as diethylenetriamine and higher homologs. In the process an alkanolamine having a primary or secondary hydroxy moiety and a primary amino group is reacted with an alkyleneamine having two amino groups and, preferably, an unbranched alkylene moiety, such as ethylenediamine. Preferably, the alkanolamine has an unbranched alkylene moiety.

The alkanolamine compounds which are used in practicing the process include those represented by the general formula:

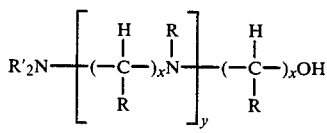

where R is hydrogen or a lower alkyl ($C_1$–$C_4$) radical, R' is hydrogen or an alkyl ($C_1$–$C_{25}$), x is a number from 2 to 6, and y is a number from 0 to 3. Exemplary of suitable alkyl radicals are the lower ($C_1$–$C_4$) alkyls, such as methyl, ethyl and butyl, and higher alkyls such as octyl, decyl and octadecyl. Methyl is the preferred lower alkyl radical. However, it is preferred that R and R' be hydrogen. Thus the alkanolamine would contain a primary amino group. Examples of alkanolamine compounds that can be used are the ethanolamines, isomeric propanolamines, N-(2-aminoethyl)ethanolamine, N-methylethanolamine, N,N-dimethylethanolamine, N,N,N'-trimethylaminoethylethanolamine and the like.

The alkyleneamine reactants that can be used in practicing the process are represented by the general formula:

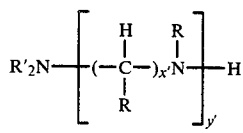

where R is a hydrogen or lower alkyl ($C_1$–$C_4$) radical, R' is hydrogen or an alkyl ($C_1$–$C_{25}$) radical, x' is a number from 2 to 6, and y' is a number from 1 to 4. Exemplary of suitable alkyl radicals are lower ($C_1$–$C_4$) alkyls, such as methyl, ethyl and butyl, and higher alkyls such as octyl, decyl and octadecyl. It is preferred that R and R' be hydrogen. The preferred lower alkyl radical is methyl. Examples of alkyleneamine compounds suited for the reaction include 1,3-propylenediamine, N-methylpropylenediamine, 1,2-propylenediamine, diethylenetriamine, N,N,N'-trimethyldiethylenetriamine, noncyclic isomers of triethylenetetramine, noncyclic isomers of tetraethylenepentamine, N-methylethylenediamine, N,N-dimethylethylenediamine and ethylenediamine which is the preferred alkyleneamine compound.

Noncyclic polyalkylene polyamines that are produced by the reaction of an alkanolamine and an alkyleneamine can be represented by the general formula:

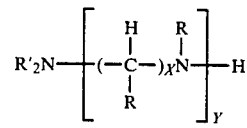

where R is hydrogen or a lower alkyl ($C_1$–$C_4$) radical, R' is hydrogen or an alkyl ($C_1$–$C_{25}$) radical, preferably a methyl radical, X is a number from 2 to 6, Y is a number from 2 to 7, and X may vary for a given value of Y. Examples of noncyclic polyalkylene polyamines that are produced include dipropylenetriamine, tributylenetetramine, di(2-methylethylene)triamine, tri(2-methylethylene)-tetramine, N-(2-aminoethyl)-1,3-propylenediamine, diethylenetriamine, and the noncyclic isomers of triethylenetetramine and tetraethylenepentamine.

One embodiment of the invention comprises a continuous process for preparing predominantly noncyclic polyalkylene polyamines by (a) adding a charge consisting essentially of an alkyleneamine compound and an alkanolamine compound to a reaction zone containing a catalytically effective amount of a Group IIA or Group IIIB metal acid phosphate at a temperature sufficient to effect a reaction between the alkanolamine compound and the alkyleneamine compound under a pressure sufficient to maintain the reaction mixture essentially in liquid phase to produce a reaction product stream containing alkanolamine compound, alkyleneamine compound and polyalkylene polyamines, and (b) withdrawing the product stream from the reaction zone and separating it to provide a polyalkylene polyamine stream and alkanolamine compound and alkyleneamine compound which are recycled to the reaction zone.

The invention can also be viewed as a method for substantially reducing the amount of alkyleneamine compound in the feed to the reaction zone in a continuous process for the preparation of predominantly noncyclic polyalkylene polyamines which continuous process comprises continuously adding a feed containing an alkanolamine compound and an alkyleneamine compound to a reaction zone containing a catalyst to yield a product stream comprising the polyamines, alkanolamine compound and alkyleneamine compound, separating the desired polyamines from the product stream and recycling the alkanolamine and alkyleneamine compounds to the reaction zone. The method of the invention would comprise (a) using a catalytically effective amount of Group IIA or Group IIIB metal acid phosphate as the catalyst, and (b) effecting the reaction under a pressure sufficient to maintain the reaction mixture substantially as a liquid phase.

The catalysts which are suited for practicing the process of the invention are Group IIA and Group IIIB metal acid phosphates including Group IIA and Group IIIB metal phosphates, monohydrogen phosphates, dihydrogen phosphates and mixtures thereof. While the intent of the catalyst preparations described hereinafter was to specifically provide a particular Group IIA or Group IIIB monohydrogen phosphate or dihydrogen phosphate, mixtures of the Group IIA or Group IIIB metal phosphates of the above-mentioned types may be obtained owing to complicated dependence of the catalyst composition on preparation conditions. Nevertheless, although the Group IIA or Group IIIB metal acid phosphate catalyst of the invention comprises the metal phosphate, monohydrogen phosphate, dihydrogen phosphates or mixtures thereof, the monohydrogen and dihydrogen phosphates of the Group IIA and Group IIIB metals would be the preferred catalysts if obtainable in relatively pure form individually or in combination.

The Group IIA metals include beryllium, magnesium, calcium, strontium and barium.

A Group IIIB metal is meant to include scandium, yttrium, lanthanum and the rare earth lanthanide metals having atomic numbers 58–71, and the rare earth actinides having atomic numbers 89 to 92.

The preferred catalysts for the production of noncyclic polyalkylene polyamines include the Group IIIB acid metal phosphates, preferably the monohydrogen phosphates and dihydrogen phosphates, of scandium, lanthanum, cerium, samarium, europium, thulium, erbium, ytterbium, yttrium, lutetium, thorium, neodymium, praseodymium, dysprosium and gadolinium.

The acid phosphate catalysts may be used for the production of polyamines either singly or in combination. As might be expected, it is preferred to use those which are more catalytically active and provide for substantial conversion to the noncyclic polyalkylene polyamine products. The preferred catalyst compounds include lanthanum monohydrogen phosphate, lanthanum dihydrogen phosphate, lanthanum phosphate, praseodymium monohydrogen phosphate, praseodymium dihydrogen phosphate, praseodymium phosphate, neodymium monohydrogen phosphate, neodymium dihydrogen phosphate, neodymium phosphate and mixtures thereof.

The quantity of the hydrogen phosphate salts of the Group IIA and Group IIIB metals used in the reaction can vary widely depending upon the reactivity of the catalysts and the reactivity of the reactants present. A catalytically effective amount of material is used; in other words, an amount which causes a reaction between the alkanolamine and the alkyleneamine to yield polyalkylene polyamine products at the temperature and pressure used. Usually though, the amount used to provide a catalytic effect ranges from about 0.1 to 25 wt% based upon alkanolamine and alkyleneamine present in the reaction mixture, and preferably in an amount of about 1.0 to 10 wt%. Within these ranges though, the level of catalysts is empirical and is adjusted depending upon the product slate desired.

In the preparation of polyalkylene polyamines the reaction is maintained at a temperature from about 200° C. to about 400° C., and preferably is carried out between 240° C. and 350° C. to obtain a practical rate of polyamine production without generation of excess levels of high molecular weight products, particularly in the reaction of monoethanolamine and ethylenediamine. The pressure utilized for carrying out the reaction is that autogenous pressure which is sufficient to maintain the reaction substantially in liquid phase, although higher pressures can be used.

Although the reactions can be carried out in the batch mode, they are also amenable to continuous process, for example operation of a continuous stirred tank reactor or a packed bed reactor. The reaction is allowed to proceed until a desired conversion is obtained or the reaction is complete. Normally the reaction is carried out within about 0.5 to 5 hours in the batch mode or residence times of 0.25 to 4.0 hours in a continuous mode for practical levels of polyamine production. For either batch or continuous processes, reaction pressure must be sufficiently high, preferably at least 100 psig, to maintain a significant portion of the reaction mixture in a liquid phase. Space velocities of 0.25 to 2.5 hr$^{-1}$, based on alkanolamine and alkyleneamine, are proposed for continuous operation. Preferred reaction times and catalyst levels depend on catalyst reactivity and are adjusted empirically. Thus, for example, relatively lower catalyst incorporations and shorter reaction times are preferred for the production of polyamines with more reactive catalysts.

Generally, to obtain the benefits of the process of the invention, the mole ratio of alkanolamine compound to alkyleneamine compound is about 1:5 to 3:1 and preferably is less than unity, such as about 1:1.5 to 1:4. Although the use of a mole ratio of alkanolamine to alkyleneamine which is less than unity in the presence of the catalysts of the invention would result in high selectivity to a noncyclic product, the disadvantage of using excess alkyleneamine compound in terms of dilution of the reaction and recovery and recycle must be taken into account.

It is preferred when reacting monoethanolamine (MEA) with ethylenediamine (EDA) that the mole ratio be in a range of 1:1.5 to 1:4 (MEA:EDA).

Recovery of the polyalkylene polyamines from the reaction mixture can be accomplished by conventional techniques, these techniques generally involving a distillation. Often a small amount of a salt, such as the one used as the catalytic material, is added to the polyalkylene polyamine separation purification as described in U.S. Pat. No. 3,755,447.

The catalysts used in the process of the invention can be prepared by the precipitation of the desired metal acid phosphate salt, washing to remove inorganic coproducts, and drying. Optionally, dried catalysts may be further processed prior to use for polyamine manufacture. Such processing is well known to those skilled in the art and may include extrusion or pelletizing, or compounding with an inert support such as alpha-alumina. Preparation of two lanthanum acid phosphates are illustrative of the general procedure by which these catalysts are made.

PREPARATION OF LANTHANUM ACID PHOSPHATE CATALYSTS

CATALYST A

Lanthanum nitrate hexahydrate (130 g, 0.30 mole) was dissolved in deionized water (150 ml) with stirring. Diammonium hydrogen phosphate (79.2 g, 0.60 mole) was dissolved in deionized water (140 ml) with stirring. While a solution of diammonium hydrogen phosphate was vigorously stirred, the solution of lanthanum nitrate was added in one portion over a period of 5 to 10 seconds. A thick, lumpy precipitate formed immediately. After 10 minutes of manual stirring, a thick, creamy suspension resulted. Vacuum filtration to isolate the precipitate was started within one-half hour of the time of addition of the solutions. Complete separation of the filtrate required 5 to 6 hours, owing to the very finely divided nature of the precipitate. The resulting pasty solid was washed sequentially with three 100 ml portions of deionized water. After washing, the filter cake was dried at 80°-90° C. to constant weight to afford 113 g of a lanthanum acid phosphate (Catalyst A).

CATALYST B

The above procedure was repeated using the following solutions to obtain 60 g of a second lanthanum acid phosphate (Catalyst B):

Ammonium dihydrogen phosphate 86.25 g (0.75 mole in 300 ml deionized water.

Lanthanum nitrate hexahydrate 108.25 g (0.25 mole) in 150 ml deionized water.

In those cases where the preparation of the Group IIIB metal acid phosphate results in a gel-like product isolation of the catalyst by filtration may be facilitated by the addition of 10 to 15% of a diatomaceous silica filter aid to the ammonium phosphate solution to form a slurry prior to adding the Group IIIB metal nitrate solution.

With regard to the preparation of a lanthanum acid phosphate catalyst, it is preferred that the lanthanum nitrate solution be prepared by diluting with water commercially available concentrated lanthanum nitrate solution having a pH of about 2 to 3. The diluted solution is then added to an aqueous ammonium phosphate solution which had been previously adjusted to a pH of about 7 with ammonium hydroxide. The final pH of the mixture should be about 6.5 where the molar ratio of the lanthanum to phosphate is about 1:3.

See also U.S. Pat. No. 3,752,878 for the preparation of rare earth metal phosphates.

The intent of the above-described lanthanum acid phosphate catalyst preparations is to provide a general procedure to prepare the desired Group IIA and IIIB metal monohydrogen phosphate or dihydrogen phosphate. However, phosphate-containing materials may be obtained which consist predominantly of the metal phosphate, the metal monohydrogen phosphate, the metal dihydrogen phosphate, or mixtures in varying proportions of the metal mono and dihydrogen phosphate, and/or mixtures in varying proportions of any of the above metal acid phosphates with the metal phosphate. Such variations in catalyst composition may result from complicated dependence of the catalyst composition on preparation conditions, such as temperature, concentration of reagents, stoichiometry of reagents, rate and order of reagent addition, pH of preparation, duration of preparation, volume and pH of waterwash, duration of catalyst washing, and duration and temperature of catalyst drying. In any event, the Group IIA and IIIB metal acid phosphates obtained according to the general preparations described above for lanthanum acid phosphates are catalytically active as exemplified for the production of polyamines in the following examples.

The following examples which illustrate the nature of the process are not intended to limit the scope of the invention. In each example the reaction was carried out at the indicated reaction temperature and times in a stirred 300 ml autoclave under that autogenous pressure which was sufficient to maintain a significant portion of the reaction in liquid phase. Such pressures ranged from 300 to 850 psig depending on the monoethanolamine:ethylenediamine feed ratio and the degree of conversion.

For purposes of brevity the products obtained are often abbreviated in the following Tables. The compound abbreviations are:

PIP—Piperazine
AEP—Aminoethylpiperazine
DETA—Diethylenetriamine
TETA(NC)—Triethylenetetramine (noncyclic isomers)
TETA(C)—Triethylenetetramine (cyclic isomers)
TEPA(NC)—Tetraethylenepentamine (noncyclic isomers)
TEPA(C)—Tetraethylenepentamine (cyclic isomers)
HVY(NC)—Pentaethylenehexamine and higher oligomeric polyethylene polyamines (noncyclic isomers)
HVY(C)—Pentaethylenehexamine and higher oligomeric polyethylene polyamines (cyclic isomers)
AEEA—Aminoethylethanolamine

EXAMPLE 1

A mixture of monoethanolamine (80.9 g, 1.33 mole), ethylenediamine (45.0 g, 0.75 mole), and strontium acid phosphate (20.0 g, 0.109 mole) was placed in a 300 ml stainless steel stirred autoclave. The mole ratio of monoethanolamine:ethylenediamine was 1.8:1.0; catalyst incorporation was 15.89 wt%, based on monoethanolamine and ethylenediamine. The mixture was heated to 300° C. for 2.0 hours during which time autogenous pressure of 440 psig developed. During the reaction the mixture was stirred at 2000 rpm. Analysis of the cooled reaction mixture by gas-liquid chromatography indicated substantial conversion of monoethanolamine and ethylenediamine to a mixture of predominantly noncyclic polyethylene amines. Additional details are set forth in Tables 1 and 2.

EXAMPLES 2-24

The above procedure was repeated with a series of Group IIA and Group IIIB metal acid phosphate catalysts A and B. Catalysts designated as "metal acid phosphate-A" were prepared from the corresponding metal nitrate and diammonium hydrogen phosphate by the procedure exemplified above for lanthanum acid phosphate catalyst A. Similarly, those catalysts designated as "metal acid phosphate-B" were prepared from the corresponding metal nitrate and ammonium dihydrogen phosphate by the procedure for lanthanum acid phosphate catalyst B. Additional experimental details and product analysis are shown in Tables 1 and 2.

TABLE 1

| Example | Catalyst | Catalyst Level (wt %)$^a$ | Temp (°C.) | Time (Hr) | Mole Ratio (MEA/EDA)$^b$ | Conversion$^c$ (%)$^d$ | Selectivity (NC)$^e$ | (AEEA)$^f$ |
|---|---|---|---|---|---|---|---|---|
| 1 | Strontium Acid Phosphate-A | 15.89 | 300 | 2 | 1.8/1.0 | 25 | 57 | 28 |
| 2 | Calcium Acid Phosphate-A | 4.47 | 300 | 2 | 2.0/1.0 | 22 | 51 | 40 |

TABLE 1-continued

| Example | Catalyst | Catalyst Level (wt %)[a] | Temp (°C.) | Time (Hr) | Mole Ratio (MEA/EDA)[b] | Conversion[c] (%)[d] | Selectivity (NC)[e] | (AEEA)[f] |
|---|---|---|---|---|---|---|---|---|
| 3 | Lanthanum Acid Phosphate-A | 7.86 | 280 | 2 | 1.8/1.0 | 30 | 54 | 28 |
| 4 | Lanthanum Acid Phosphate-A | 7.86 | 300 | 2 | 1.8/1.0 | 47 | 66 | 16 |
| 5 | Lanthanum Acid Phosphate-A | 8.28 | 300 | 2 | 2.5/1.0 | 44 | 55 | 23 |
| 6 | Yttrium Acid Phosphate-A | 6.54 | 300 | 2 | 1.8/1.0 | 56 | 54 | 17 |
| 7 | Neodymium Acid Phosphate-A | 8.08 | 300 | 2 | 1.8/1.0 | 64 | 54 | 17 |
| 8 | Cerium Acid 1/2 | 7.99 | 300 | 2 | 1.8/1.0 | 52 | 58 | 24 |
| 9 | Praseodymium Acid Phosphate-A | 7.86 | 280 | 2 | 1.8/1.0 | 40 | 57 | 28 |
| 10 | Praseodymium Acid Phosphate-A | 7.87 | 300 | 2 | 1.8/1.0 | 44 | 62 | 16 |
| 11 | Praseodymium Acid Phosphate-A | 3.69 | 300 | 1 | 3.0/1.0 | 40 | 51 | 31 |
| 12 | Samarium Acid Phosphate-A | 8.07 | 300 | 2 | 1.8/1.0 | 51 | 63 | 17 |
| 13 | Mixed Metal Acid Phosphates-A[g] | 7.86[h] | 300 | 2 | 1.8/1.0 | 45 | 62 | 16 |
| 14 | Lanthanum Acid Phosphate-B | 2.99 | 300 | 2 | 1.8/1.0 | 55 | 60 | 12 |
| 15 | Lanthanum Acid Phosphate-B | 5.95 | 300 | 2 | 1.8/1.0 | 78 | 55 | 11 |
| 16 | Praseodymium Acid Phosphate-B | 5.95 | 300 | 2 | 1.8/1.0 | 45 | 60 | 14 |
| 17 | Thorium Acid Phosphate-B | 3.12 | 300 | 2 | 1.8/1.0 | 54 | 61 | 9 |
| 18 | Samarium Acid Phosphate-B | 3.14 | 300 | 2 | 1.8/1.0 | 39 | 60 | 16 |
| 19 | Dysprosium Acid Phosphate-B | 3.07 | 300 | 2 | 1.8/1.0 | 42 | 61 | 15 |
| 20 | Gadolinium Acid Phosphate-B | 3.14 | 300 | 2 | 1.8/1.0 | 36 | 62 | 20 |
| 21 | Lanthanum Acid Phosphate-A | 7.49 | 300 | 2 | 1/2 | 46 | 88 | 6 |
| 22 | Lanthanum Acid Phosphate-A | 8.31 | 300 | 2 | 1/4 | 51 | 95 | 3 |
| 23 | Praseodymium Acid Phosphate-B | 5.63 | 300 | 2 | 1/2 | 34 | 81 | 15 |
| 24 | Samarium Acid Phosphate-B | 5.64 | 300 | 2 | 1/2 | 39 | 82 | 14 |

[a]Based on monoethanolamine and ethylenediamine.
[b]Mole ratio of monoethanolamine:ethylenediamine in the feedstock.
[c]Derived from analyses presented in Table 2; all results are rounded off to the nearest integer.
[d]Based on unchanged monoethanolamine and ethylenediamine.
[e]Weight percent of linear and branched polyethylene amines in the total polyamine product.
[f]Weight percent aminoethylethanolamine in the total polyamine product.
[g]Weight ratio of lanthanum:cerium:praseodymium:neodymium in the catalyst is 8.49:2.05:1.00:2.94.
[h]Based on total rare earth hydrogen phosphate.

TABLE 2

| Example | PIP | AEP | DETA | TETA(NC) | TETA(C) | TEPA(NC) | TEPA(C) | HVY(NC) | HVY(C) | AEEA |
|---|---|---|---|---|---|---|---|---|---|---|
| 1 | 7.01 | 5.14 | 38.99 | 17.64 | 3.17 | 0.00 | 0.00 | 0.00 | 0.00 | 28.05 |

TABLE 2-continued

| Example | PIP | AEP | DETA | TETA(NC) | TETA(C) | TEPA(NC) | TEPA(C) | HVY(NC) | HVY(C) | AEEA |
|---|---|---|---|---|---|---|---|---|---|---|
| 2 | 4.41 | 3.27 | 44.37 | 3.42 | 1.67 | 3.27 | 0.00 | 0.00 | 0.00 | 38.57 |
| 3 | 9.12 | 4.99 | 34.50 | 16.46 | 3.56 | 3.02 | 0.00 | 0.00 | 0.00 | 28.26 |
| 4 | 4.56 | 5.47 | 31.43 | 26.02 | 4.08 | 8.26 | 3.67 | 0.00 | 0.00 | 15.76 |
| 5 | 4.38 | 7.21 | 30.69 | 12.70 | 6.01 | 11.85 | 4.21 | 0.00 | 0.00 | 22.96 |
| 6 | 4.23 | 8.33 | 27.87 | 12.32 | 6.81 | 9.57 | 4.13 | 4.09 | 5.16 | 17.48 |
| 7 | 4.66 | 7.95 | 25.10 | 13.53 | 8.13 | 11.53 | 5.29 | 3.66 | 2.66 | 17.49 |
| 8 | 4.53 | 6.59 | 30.84 | 14.84 | 4.73 | 10.69 | 2.15 | 1.10 | 0.48 | 24.06 |
| 9 | 3.78 | 6.98 | 39.77 | 11.60 | 3.39 | 5.15 | 1.56 | 0.00 | 0.00 | 27.77 |
| 10 | 4.78 | 6.72 | 32.96 | 13.77 | 7.08 | 13.80 | 3.27 | 2.01 | 0.00 | 15.60 |
| 11 | 4.36 | 7.18 | 30.37 | 11.14 | 4.02 | 9.53 | 2.30 | 0.00 | 0.00 | 31.11 |
| 12 | 4.49 | 6.58 | 32.78 | 14.06 | 4.62 | 13.68 | 4.66 | 2.52 | 0.00 | 16.62 |
| 13 | 4.99 | 6.65 | 33.51 | 13.19 | 5.73 | 11.75 | 3.95 | 3.51 | 0.74 | 16.00 |
| 14 | 4.90 | 6.89 | 26.76 | 13.23 | 7.13 | 15.25 | 6.85 | 5.21 | 2.23 | 11.55 |
| 15 | 5.30 | 8.40 | 18.02 | 15.22 | 7.21 | 16.99 | 6.61 | 4.36 | 7.14 | 10.74 |
| 16 | 4.48 | 7.94 | 31.07 | 13.48 | 7.38 | 12.55 | 4.91 | 3.23 | 0.79 | 14.17 |
| 17 | 4.45 | 7.38 | 27.90 | 12.73 | 9.11 | 14.57 | 7.27 | 5.62 | 2.46 | 8.51 |
| 18 | 5.30 | 7.25 | 31.86 | 12.99 | 6.36 | 11.43 | 4.10 | 3.43 | 0.82 | 16.46 |
| 19 | 5.13 | 7.40 | 31.96 | 14.18 | 7.09 | 11.20 | 4.00 | 3.21 | 0.74 | 15.08 |
| 20 | 4.65 | 6.98 | 35.12 | 12.97 | 4.47 | 12.12 | 2.10 | 1.39 | 0.00 | 20.17 |
| 21 | 4.26 | 1.90 | 67.59 | 20.09 | 0.0 | 0.0 | 0.0 | 0.0 | 0.0 | 6.16 |
| 22 | 1.40 | 0.77 | 88.44 | 6.16 | 0.0 | 0.0 | 0.0 | 0.0 | 0.0 | 3.23 |
| 23 | 2.59 | 0.86 | 73.49 | 7.59 | 0.0 | 0.0 | 0.0 | 0.0 | 0.0 | 15.47 |
| 24 | 2.69 | 1.31 | 71.27 | 10.91 | 0.0 | 0.0 | 0.0 | 0.0 | 0.0 | 13.81 |

Weight % of products is expressed on a feedstock-free, water-free, weight-normalized basis.

COMPARATIVE EXAMPLE 25

A mixture of monoethanolamine (91.5 g, 1.50 mole), ethylenediamine (45.0 g, 0.75 mole), and boron phosphate (4.8 g, 0.045 mole) was placed in a 300 ml stainless steel autoclave. The mole ratio of monoethanolamine:ethylenediamine was 2:1; catalyst incorporation was 3.52 wt%, based on monoethanolamine and ethylenediamine. Reaction was carried out at 300° C. for 2.0 hours according to the procedure of Example 1. Analysis of the cooled reaction mixture by gas-liquid chromatography indicated that a mixture of predominantly cyclic polyethyleneamines had been formed (see Tables 3 and 4).

COMPARATIVE EXAMPLE 26

The procedure of Comparative Example 25 was repeated with a reaction time of only 1 hour. Analysis of the cooled reaction mixture by gas-liquid chromatography indicated that a mixture of predominently cyclic polyethylene polyamines had been formed (See Tables 3 and 4).

COMPARATIVE EXAMPLE 27

The procedure of Comparative Example 25 was repeated with inclusion of a higher level of boron phosphate (12.5 g, 0.1182 mole; 9.16 wt%, based on monoethanolamine and ethylenediamine). Analysis of the cooled reaction mixture by gas-liquid chromatography indicated that a mixture of predominently cyclic polyethylene polyamines had been formed (See Tables 3 and 4).

COMPARATIVE EXAMPLE 28

A mixture of monoethanolamine (80.9 g, 1.33 mole), ethylenediamine (45.0 g, 0.75 mole), and disodium hydrogen phosphate (15.9 g, 0.112 mole) was placed in a 300 ml stainless steel stirred autoclave. The mole ratio of monoethanolamine:ethylenediamine was 1.8:1.0; catalyst incorporation was 12.63 wt%, based on monoethanolamine and ethylenediamine. Reaction was carried out at 300° C. for 2.0 hours according to the procedure of Example 1. Analysis of the cooled reaction mixture by gas-liquid chromatography indicated that essentially no polyethylene polyamines had been formed (See Tables 3 and 4).

COMPARATIVE EXAMPLE 29

A mixture of monoethanolamine (46.0 gm, 0.75 mole), ethylenediamine (92.0 gm, 1.53 mole), and boron phosphate (12.0 gm; 8.70 weight %, based on monoethanolamine and ethylenediamine) was placed in a 300 ml stainless steel autoclave. The mole ratio of monoethanolamine:ethylenediamine was 1:2. Reaction was carried out at 300° C. for 2.0 hours according to the procedure of Example 1. Analysis of the cooled reaction mixture by gas-liquid chromatography indicated that a mixture of predominantly cyclic polyethyleneamines had been formed (see Tables 3 and 4).

TABLE 3

| Comparative Example | Catalyst | Catalyst Level (wt %)[a] | Temp (°C.) | Time (Hr) | Mole Ratio (MEA/EDA)[b] | Conversion[c] (%)[d] | Selectivity[c] (NC)[e] |
|---|---|---|---|---|---|---|---|
| 25 | Boron Phosphate | 3.52 | 300 | 2 | 2.0/1.0 | 80 | 33 |
| 26 | Boron Phosphate | 3.52 | 300 | 1 | 2.0/1.0 | 72 | 46 |
| 27 | Boron Phosphate | 9.16 | 300 | 2 | 2.0/1.0 | 95 | 9 |
| 28 | Disodium Hydrogen Phosphate | 12.63 | 300 | 2 | 1.8/1.0 | 1 | 15 |
| 29 | Boron Phosphate | 8.70 | 300 | 2 | 1.0/2.0 | 97 | 44 |

[a]Based on monoethanolamine and ethylenediamine.
[b]Mole ratio of monoethanolamine:ethylenediamine in the feedstock.
[c]Derived from analyses presented in Table 4; all results are rounded off to the nearest integer.
[d]Based on unchanged monoethanolamine and ethylenediamine.
[e]Weight percent of linear and branched polyethylene amines in the total polyamine product.

TABLE 4

| Comparative Example | PIP | AEP | DETA | TETA(NC) | TETA(C) | TEPA(NC) | TEPA(C) | HVY(NC) | HVY(C) | AEEA |
|---|---|---|---|---|---|---|---|---|---|---|
| 25 | 11.19 | 16.11 | 14.29 | 12.06 | 23.61 | 5.49 | 10.50 | 1.56 | 4.12 | 1.06 |
| 26 | 4.16 | 8.55 | 13.69 | 11.39 | 15.60 | 14.81 | 13.80 | 5.68 | 9.90 | 2.42 |
| 27 | 10.08 | 11.48 | 3.38 | 0.89 | 18.66 | 1.33 | 14.41 | 2.98 | 36.46 | 0.34 |
| 28 | 24.24 | 0.00 | 15.15 | 0.00 | 0.00 | 0.00 | 0.00 | 0.00 | 0.00 | 60.60 |
| 29 | 16.42 | 21.14 | 25.37 | 11.19 | 10.45 | 7.21 | 8.22 | 0.00 | 0.00 | N.D. |

Weight % of products is expressed on a feedstock-free, water-free, weight-normalized basis.
N.D. = not detected.

As can be readily seen from the data set forth in the above Tables, under comparable conditions of reaction time, feed composition and reaction temperature, catalysts that incorporate Group IIIB metals provide higher conversions of monoethanolamine and ethylenediamine to noncyclic polyamines than the corresponding catalysts based on Group IIA metals. Compare Examples 1 and 2 with Examples 4, 6–8, 10, and 12–20. In turn, catalysts that incorporate Group IIA metals provide higher conversions of monoethanolamine and ethylenediamine to noncyclic polyamines than the prior art catalysts boron phosphate and disodium hydrogen phosphate (Comparative Examples 25–29).

Examples 3 and 4, and 9 and 10 demonstrate that conversion of monoethanolamine and ethylenediamine to polyamines increases as the reaction temperature is increased at a fixed catalyst incorporation, reaction time and feed composition. Concurrently, selectivity to noncyclic polyamines increases while selectivity to aminoethylethanolamine decreases. Production of noncyclic polyamines at the expense of aminoethylethanolamine at the higher temperatures may result from the conversion of aminoethylethanolamine to noncyclic polyamines by intermolecular alkylation of ethylenediamine.

As the level of catalyst incorporation is increased at a fixed reaction temperature, residence time and feed composition, Examples 14 and 15 show that a higher conversion of ethylenediamine and monoethanolamine to polyamines is obtained. However, selectivity to noncyclic polyamines decreases slightly.

With an increased mole ratio of monoethanolamine to ethylenediamine in the feed at a fixed reaction temperature, residence time and catalyst level, the rate of self-condensation of monoethanolamine to form aminoethylethanolamine increases, and selectivity to noncyclic polyamines decreases. (See Examples 4 and 5). Even under conditions which favor lower conversions and thus higher selectivities to noncyclic polyamines, e.g. at a shorter residence time and with a lower catalyst incorporation, higher selectivity to aminoethylethanolamine and lower production of noncyclic polyamines result from an increased concentration of monoethanolamine in the feed. Thus Examples 10 and 11 suggest that the maximum molar ratio of alkanolamine to alkyleneamine for the production of noncyclics is about 3.5:1.

Examples 21–24 show that greatest selectivities to noncyclic polyamines are obtained from mixtures of monoethanolamine and ethylenediamine in which the molar ratio of monoethanolamine:ethylenediamine is less than 1, for example, when the mole ratio ranges from 1:2 to 1:5.

This invention is a process for the production of predominantly noncyclic polyethylene polyamines from mixtures of monoethanolamine and ethylenediamine in which the mole ratio of monoethanolamine:ethylenediamine is from 1:5 to 3:1. Preferably, the mole ratio of monoethanolamine:ethylenediamine is less than unity for maximum production of noncyclic polyamines. However, predominantly noncyclic polyamine products are also obtained when the mole ratio of monoethanolamine:ethylenediamine is greater than unity, but less than about 3.5:1.

The prior art methods for the production of the more commercially desirable noncyclic polyamines possess certain deficiencies. Reductive amination not only produces only small quantities of triethylenetetramine and higher polyamines from ethylenediamine and monoethanolamine, but also is typically operated with inclusion of significant quantities of water in the feedstock, for example 25–50 wt%, based on combined ethylenediamine and monoethanolamine. Production of noncyclic polyamines from ethylenediamine and monoethanolamine by the phosphorus containing catalysts of the prior art requires reaction of a molar excess of ethylenediamine with a molar deficiency of monoethanolamine in order to obtain predominently noncyclic products. Inclusion of water or excess ethylenediamine dilutes the reaction, increases the size of equipment needed to produce a given quantity of polyamines and complicates product isolation and purification.

In contrast, a preferred process of this invention involves reaction of a molar deficiency of ethylenediamine with a molar excess of monoethanolamine in the presence of certain acid phosphate catalysts to produce predominantly noncyclic polyamines. A wide range of noncyclic polyamines is produced without the necessity of including an inert diluent or excess ethylenediamine in the feed and removing it from the product.

STATEMENT OF INDUSTRIAL APPLICATION

The inventive process for preparing predominently noncyclic polyalkylene polyamine compounds is applicable to the preparation of noncyclic polyethylene polyamines which are extensively used in a wide variety of applications. Significant uses of polyethylene polyamines include their use as corrosion inhibitors, fabric softeners, lubricating oil additives, co-monomers for polyamide resins, fungicides, surfactants, curing agents for epoxy resins and chelating agents.

We claim:

1. A process for preparing predominantly noncyclic polyalkylene polyamines which comprises:
   contacting an alkanolamine compound having an amino group and a primary or secondary hydroxy group with an alkyleneamine compound having two amino groups in the presence of a catalytically effective amount of a catalyst consisting essentially of a Group IIA or Group IIIB metal acid phosphate at a temperature sufficient to effect the reaction between the alkanolamine compound and the alkyleneamine compound under a pressure sufficient to maintain the reaction mixture essentially in liquid phase.

2. The process of claim 1 in which the alkanolamine:alkyleneamine molar ratio is about 1:5 to 3:1.

3. The process of claim 1 in which the the alkanolamine:alkyleneamine molar ratio is less than one.

4. The process of claim 1 in which the catalyst is a Group IIIB metal acid phosphate.

5. The process of claim 4 in which the Group IIIB metal is scandium, yttrium, lanthanum or a rare earth lanthanide having an atomic number from 58 to 71.

6. The process of claim 5 in which the catalyst is a Group IIIB metal monohydrogen phosphate.

7. The process of claim 1 in which the catalyst is a monohydrogen phosphate salt of strontium, calcium, lanthanum, yttrium, neodymium, cerium, praseodymium or samarium.

8. The process of claim 5 in which the catalyst is a Group IIIB dihydrogen phosphate.

9. The process of claim 8 in which the catalyst is a dihydrogen phosphate salt of lanthanum, praseodymium, thorium, samarium, dysprosium or gadolinium.

10. The process of claim 1 in which the temperature is from about 200° C. to 400° C. and the molar ratio of alkanolamine to alkyleneamine is from 1:2 to 1:5.

11. The process of claim 10 in which the catalyst is lanthanum acid phosphate.

12. The process of claim 1 in which the catalyst is present from 0.1 to 25 wt% base upon alkanolamine and alkyleneamine.

13. A process for preparing a noncyclic polyalkylene polyamine which comprises:
    (a) contacting an alkanolamine compound having a primary amino group and a primary or secondary hydroxyl group of the general formula

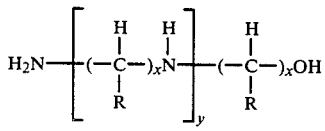

where R is hydrogen or a lower alkyl ($C_1$-$C_4$) radical, x is a number from 2 to 6, and y is a number from 0 to 3, and an alkyleneamine compound having two primary amino groups of the general formula:

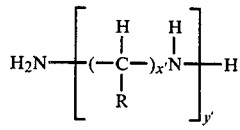

where R is hydrogen or a lower alkyl ($C_1$-$C_4$) radical, x' is a number from 2 to 6, and y' is a number from 1 to 4, in an alkanolamine compound:alkyleneamine compound molar ratio from 1:2 to 1:5, in the presence of a catalytically effective amount of a catalyst consisting essentially of an acid phosphate salt of a Group IIA or Group IIIB metal at a temperature from about 240° C. to about 350° C. under a pressure sufficient to maintain the reaction mixture substantially in liquid phase, and
    (b) recovering the noncyclic polyalkylene polyamine from the resultant reaction mixture.

14. The process of claim 13 in which the catalyst is an acid phosphate salt of a Group IIIB metal selected from the group consisting of scandium, yttrium, lanthanum and the rare earth lanthanides having an Atomic Number from 58 to 71.

15. The process of claim 14 in which the alkanolamine is an ethanolamine when R is hydrogen or a lower alkyl ($C_1$-$C_4$) radical, x is 2 and y is 0 to 3, and the alkyleneamine is an ethyleneamine when R is hydrogen or a lower alkyl ($C_1$-$C_4$) radical, x' is 2 and y' is 1 to 4.

16. The process of claim 15 in which the alkanolamine is monoethanolamine and the ethyleneamine is ethylenediamine.

17. The process of claim 16 in which the catalyst is a Group IIIB monohydrogen phosphate.

18. The process of claim 17 in which the catalyst is a monohydrogen phosphate salt of lanthanum, neodymium or praseodymium.

19. The process of claim 16 in which the catalyst is a Group IIIB dihydrogen phosphate.

20. The process of claim 19 in which the catalyst is a dihydrogen phosphate salt of lanthanum, neodymium or praseodymium.

21. A process for preparing a noncyclic polyalkylene polyamine which comprises:
    contacting an alkanolamine compound having an amino group and a primary or secondary hydroxy group of the general formula:

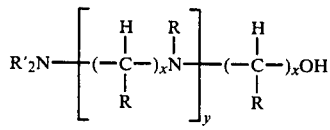

where R is hydrogen or a lower alkyl ($C_1$-$C_4$) radical, R' is hydrogen or an alkyl ($C_1$-$C_{25}$) radical, x is a number from 2 to 6, and y is a number from 0 to 3 with an alkyleneamine compound having two amino groups of the general formula:

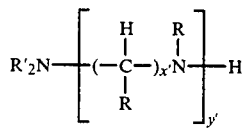

where R is a hydrogen or a lower alkyl ($C_1$-$C_4$) radical, R' is hydrogen or an alkyl ($C_1$-$C_{25}$) radical, x' is a number from 2 to 6, and y' is a number from 1 to 4 in the presence of a catalytically effective amount of a catalyst consisting essentially of an acid phosphate salt of a Group IIA or Group IIIB metal at a temperature from about 175° C. to about 400° C. under a pressure sufficient to maintain the reaction mixture essentially in liquid phase.

22. The process of claim 21 in which the catalyst is a Group IIIB metal monohydrogen phosphate.

23. The process of claim 21 in which the catalyst is a Group IIIB metal dihydrogen phosphate.

24. A continuous process for preparing predominantly noncyclic polyalkylene polyamines which comprises
    (a) adding a charge consisting essentially of an alkyleneamine compound having two amino groups and an alkanolamine compound having an amino group and a primary or secondary hydroxy group to a reaction zone containing a catalytically effective amount of a catalyst consisting essentially of a Group IIA or IIIB metal acid phosphate at a temperature sufficient to effect a reaction between the alkanolamine compound and the alkyleneamine compound under a pressure sufficient to maintain the reaction mixture essentially in liquid phase to produce a reaction product stream comprising alkanolamine compound, alkyleneamine compound and polyalkylene polyamines, and (b) withdrawing the product stream from the reaction zone and separating it to provide a polyalkylene polyamines stream and alkanolamine compound and alkyleneamine compound which are recycled to the reaction zone.

25. The process of claim 24 in which the charge consists essentially of monoethanolamine and ethylenediamine.

26. The process of claim 25 in which the molar ratio of monoethanolamine:ethylenediamine in the reaction zone is maintained from 1:5 to 3:1 and the pressure is from about 5 to 150 atmospheres.

27. The process of claim 24 in which the catalyst is a lanthanum acid phosphate.

28. The process of claim 26 in which the catalyst is a lanthanum acid phosphate.

29. In a continuous process for the preparation of predominantly noncyclic polyalkylene polyamines which comprises continuously adding a feed comprising an alkanolamine compound having a primary amino group and a primary or secondary hydroxy group and an alkyleneamine compound having two primary amino groups to a reaction zone containing a catalyst to yield a product stream comprising noncyclic polyalkylene polyamines, alkanolamine compound and alkyleneamine compound, separating the desired polyamines from the product stream and recycling the alkanolamine and alkyleneamine compounds to the reaction zone, the method for substantially reducing the amount of alkyleneamine compound in the feed to the reaction zone, which method comprises (a) adding a feed comprising a molar ratio of alkanolamine compound:alkyleneamine compound less than one,
(b) using a catalytically effective amount of a catalyst consisting essentially of a Group IIA or Group IIIB metal acid phosphate as the catalyst, and
(c) effecting the reaction under a pressure sufficient to maintain the reaction mixture essentially in liquid phase.

30. The method of claim 29 in which the catlyst is a Group IIIB metal acid phosphate.

31. The method of claim 30 in which the alkanolamine compound is monoethanolamine and the alkyleneamine compound is ethylenediamine.

32. The method of claim 31 in which the molar ratio of monoethanolamine:ethylenediamine in the reaction zone is from 1:2 to 1:5.

33. The method of claim 32 in which the catalyst is a lanthanum acid phosphate.

34. The method of claim 33 in which the pressure is from about 5 to 150 atmospheres.

35. The method of claim 34 in which the temperature is from 200° C. to 400° C.

36. The process of claim 1 in which the catalyst is a mixture of the Group IIIB metal phosphate, monohydrogen phosphate and dihydrogen phosphate.

37. The process of claim 16 in which the catalyst is a mixture of the Group IIIB metal phosphate, monohydrogen phosphate and dihydrogen phosphate.

38. The process of claim 21 in which the catalyst is a mixture of the Group IIIB metal phosphate, monohydrogen phosphate and dihydrogen phosphate.

39. The process of claim 24 in which the catalyst is a mixture of the Group IIIB metal phosphate, monohydrogen phosphate and dihydrogen phosphate.

40. The process of claim 29 in which the catalyst is a mixture of the Group IIIB metal phosphate, monohydrogen phosphate and dihydrogen phosphate.

* * * * *